United States Patent [19]

Beck

[11] Patent Number: Plant 7,700

[45] Date of Patent: Nov. 5, 1991

[54] ORANGE TREE 'BECK EARLY NAVEL'

[76] Inventor: James W. Beck, 2118 9th Ave., Delano, Calif. 93215

[21] Appl. No.: 549,545

[22] Filed: Jul. 5, 1990

Related U.S. Application Data

[63] Continuation of Ser. No. 356,680, May 24, 1989, abandoned, which is a continuation of Ser. No. 623,223, Jun. 21, 1984, abandoned.

[51] Int. Cl.[5] ..... A01H 5/00

[52] U.S. Cl. ..... Plt./45

[58] Field of Search ..... Plt. 45

[56] References Cited

U.S. PATENT DOCUMENTS

P.P. 1,26 5/1935 Robertson ..... Plt. 45

P.P. 2,818 7/1968 Mabs ..... Plt. 45

P.P. 2,970 6/1970 Walker et al. ..... Plt. 45

OTHER PUBLICATIONS

Mortensen, E. et al., "Orange-Sour and Orange-Sweet", *Handbook of Tropical and Subtropical Horticulture,* Dept. of State, AID, Wash., D.C., 1970, pp. 47-50.

Soost, R. K. et al., "Citrus" *Advances in Fruit Breeding,* Purdue Univ. Press, West Lafayette, Ind. 1975, pp. 507-541.

*Primary Examiner*—James R. Feyrer

*Attorney, Agent, or Firm*—Kelly Bauersfeld & Lowry

[57] ABSTRACT

The new orange tree is characterized by a somewhat smaller tree size as compared to other navel varieties, early maturity and a distinct red-orange color of the fruit and wherein the rind of the fruit is very durable.

4 Drawing Sheets

This application is a continuation of application Ser. No. 356,680 filed May 24, 1989, abandoned, which is a continuation of application Ser. No. 623,223 filed June 21, 1984, abandoned.

This invention relates to a new and distinct variety of navel orange tree and is characterized by the approximately one-third smaller tree size as compared to a conventional Washington navel (unpatented) variety.

The tree itself is the result of a sport discovered in a planting of navels located Southeast of Delano, Calif. A reproduction of this tree was made by removing a bud from the sport and placing it in a seedling of Troyer Citrange root stock. The asexual reproduction of this tree by budding has resulted in an orange with an early maturity date of about October 10 to October 15 in comparison with Bonanza navel orange tree, another relatively early bearing variety which has a maturity date of about October 15 to October 21. In addition, the orange has a distinctive bright red orange color. Observations of this new tree may be made at the Beck Ranch in Delano, Calif.

In the accompanying photographs,

Figure 1:
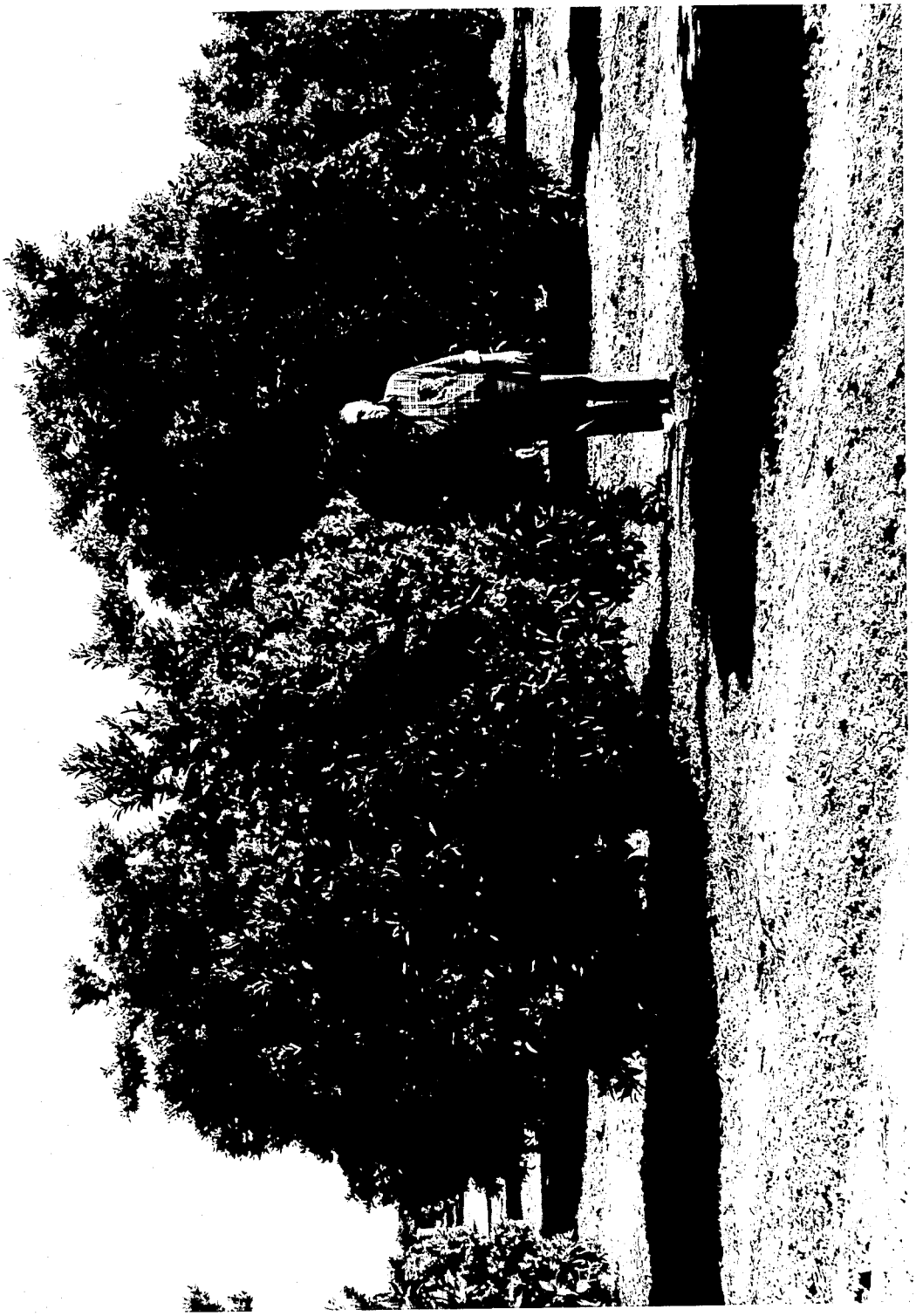
FIG. 1 shows the size of an overall orange tree of the present new and dintinct variety at the left as compared to a conventional Washington navle orange tree shown behind and to the right.
Figure 2:
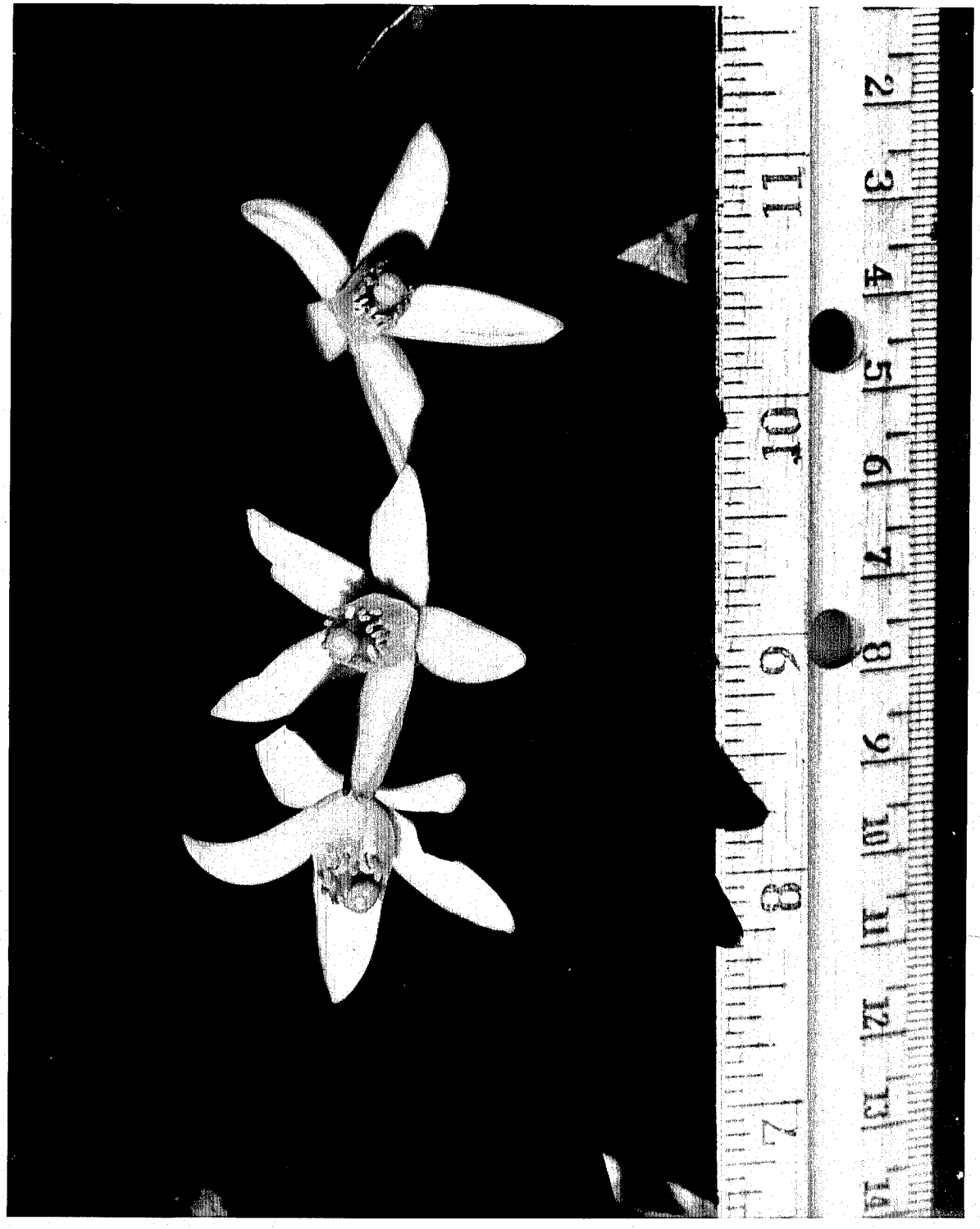
FIG. 2 is a greatly enlarged view of the foliage wherein the shape and texture of the leaf and blossoms are evident.
Figure 3:
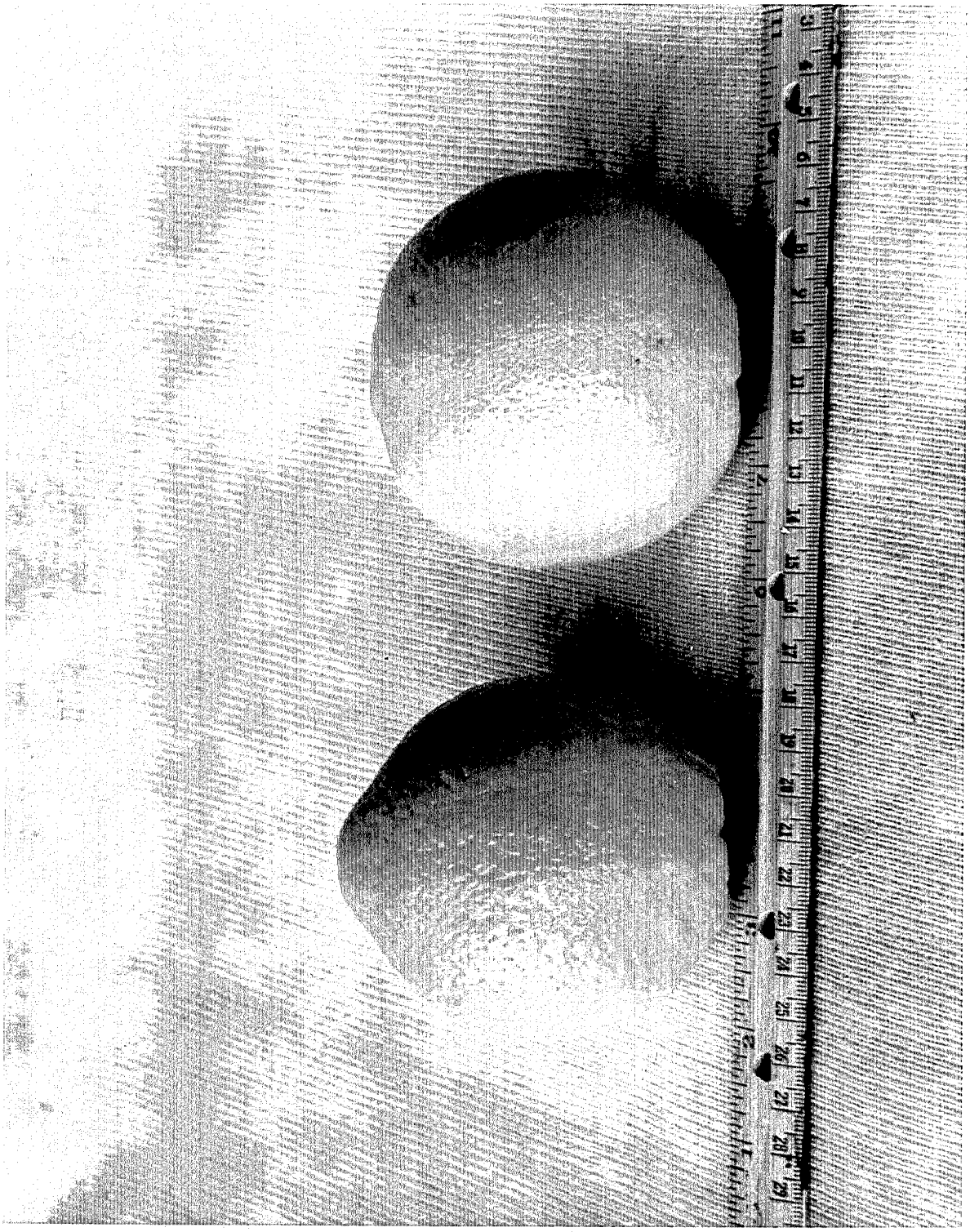
FIG. 3 shows an example of the fruit to the left compared with a conventional Washington navel orange shown on the right. The somewhat ovoid configuration as well as the red-orange color of the new and distinct variety of orange of the present invention compared to the conventional Washington navel orange on the right will be evident.
Figure 4:
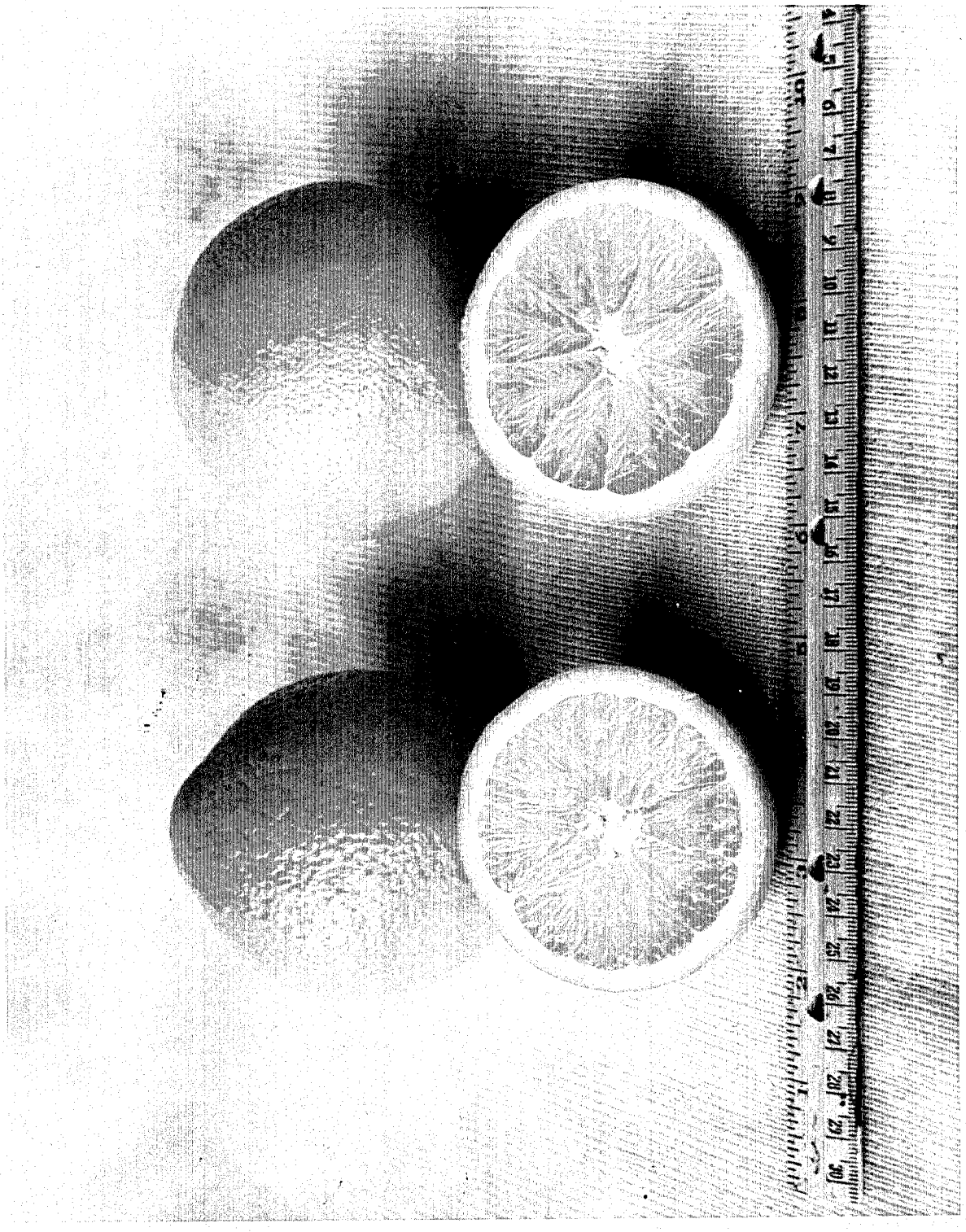
FIG. 4 is a view similar to FIG. 3 of the new and distinct variety of orange of the present invention compared to a conventional Washington navel orange further illustration a cross section of the orange wherein it will be evident that both are seedless.

Following is an outline description in greater detail of the distinct variety of orange tree of this invention:

PLANT

Form: Tree.

Growth: Vigorous, approximately one foot per year to a mature size approximately one-third smaller than a Washington navel orange tree.

Wood:

*New wood.*—Color — Dark green. Bark — smooth.

*Old wood.*—Color — Brown. Bark — smooth.

Foliage: Single leaf.

*Size.*—Large leaves, very similar in size to the leaves of a Washington navel orange tree.

*Quantity.*—Abundant, slightly denser than the leaves of a Washington navel orange tree.

*Color.*—New foliage — Upper side — dark green. Underside — light green. Old foliage: Upper side — dark green. Underside — light green. The upper side of the Beck Navel leaf had a Munsell color measurement of 4.4 YR 3.6/2.6 whereas the Munsell measurement for a Washington navel averaged 4.5 YR 3.6/2.7. The underside of the Beck leaf averaged 7.9 YR 4.6/3.9; the Washington Navel 7.2 YR 4.8/4.2.

*Shape.*—Oval, pointed.

*Texture.*—Upper side — glossy. Under side — smooth.

*Ribs and veins.*—Ordinary.

*Edge.*—Smooth.

*Leaf stem color.*—Green.

Fruit: Very good quality. Variety is fertile with its own pollen.

*Form.*—Ovoid or oblong, often referred to as "sheep-nosed." The Washington Navel is nearly spheroidal.

*Aspect.*—Smooth.

*Color at maturity.*—Red-orange. The color chart designation, *Dictionary of Color,* Maerz and Paul, First Edition, 1930 is "flash" (K-11) for the rind and "orange peel" (L-10) for the meat. The Washington Navel meat is Scarlet Vermillion, I-12-Plate 2, page 27. Generally speaking, there is no standard color for either the Back Navel or Washington Navel because varieties become more reddish as the season advances until about August when they may re-green somewhat.

*Size at maturity.*—Large, averaging about 3.04 to about 3.30 inches in diameter. As compared with the Washington Navel, no difference in average size has been established.

*Seeds.*—None viable.

Blooming habit: Blooms once profusely in the spring. The blossoms are generally indistinguishable from the blossoms of a Washington navel orange tree.

*Time of bloom.*—The bloom of the Beck Navel and the Washington Navel each begins at the end of March or the beginning of April and lasts through April.

Caltivar name: "Beck early navel orange tree".

Rind oil glands: The oil glands contrast with many citrus fruit varieties including those of Bonanza Navels. However, under ordinary field conditions, the rind oil glands of Beck Navels are objectively indistinguishable from those of Washington or Fisher Navels.

Harvesting: Beck Navels are normally harvested about four weeks in advance of Washington Navels grown under equal environmental conditions.

Ripening: Both the Beck Navel and the Washington Navel become ripe on the tree and both enjoy favorable tree storage characteristics on the tree during an extended season. In practice, Becks are not normally held late on the trees because they bring premium prices since they are ready earlier than Washington Navels.

Fruit Peeling (rind): Both the Beck Navel and the Washington Navel peel easily when harvested during the heart of their seasons and under favorable environmental conditions. In the San Joaquin Valley in Central California, the thickness of the peel is thinner than it is in the coastal regions and thicker than in the hotter regions. The peel of the Beck Navel is thicker than the Bonanza Navel in the San Joaquin Valley, but considered to be the same as the Washington Navel.

Taste: At any given time of year, when typical fruits are simultaneously harvested, the Beck Navel will be sweeter and have less of an acid component than the Washington Navel.

As shown in the accompanying photographs of the Figures, this tree is somewhat smaller (approximately one-third smaller) in size than the conventional navel tree. When the fruit is picked early before full rind color has developed and the fruit is gassed to induce color, full color will occur. The rind of this fruit is very durable and will withstand such abuse as occurs during harvesting and shipping.

Sugar/acid content ratio figures indicating sweetness of the orange increase more rapidly with the new and distinct variety of orange of this invention as compared to a conventional navel orange.

The tree and its fruit herein described may vary in slight detail due to climatic or soil conditions under which the variety is grown.

I claim:

1. A new and distinct variety of orange tree substantially as shown and described, characterized particularly as to novelty by a somewhat smaller tree size that the conventional Washington navel tree, a bright red-orange color of the fruit with a more durable rind than a conventional Washington navel orange and maturing during a relatively shorter period.

* * * * *